(12) United States Patent
Zink et al.

(10) Patent No.: US 11,123,196 B1
(45) Date of Patent: Sep. 21, 2021

(54) STAND ALONE METATARSOPHALANGEAL (MTP) JOINT FUSION DEVICE

(71) Applicants: Thomas Zink, San Antonio, TX (US); Kyle Vaughn, Phoenix, AZ (US); Alexandra Zink, San Antonio, TX (US)

(72) Inventors: Thomas Zink, San Antonio, TX (US); Kyle Vaughn, Phoenix, AZ (US); Alexandra Zink, San Antonio, TX (US)

( * ) Notice: Subject to any disclaimer, the term of this patent is extended or adjusted under 35 U.S.C. 154(b) by 0 days.

(21) Appl. No.: 16/869,073

(22) Filed: May 7, 2020

(51) Int. Cl.
| | |
|---|---|
| A61F 2/42 | (2006.01) |
| A61F 2/30 | (2006.01) |
| A61B 17/72 | (2006.01) |

(52) U.S. Cl.
CPC ........ A61F 2/4225 (2013.01); A61B 17/7291 (2013.01); A61F 2/30942 (2013.01); *A61F 2002/3085* (2013.01); *A61F 2002/3093* (2013.01); *A61F 2002/30227* (2013.01); *A61F 2002/30578* (2013.01); *A61F 2002/30622* (2013.01); *A61F 2002/4233* (2013.01); *A61F 2310/00023* (2013.01)

(58) Field of Classification Search
CPC ............ A61F 2/4225; A61F 2002/4233; A61F 2002/4228; A61F 2002/4238; A61F 2002/4251; A61B 17/7291
See application file for complete search history.

(56) References Cited

U.S. PATENT DOCUMENTS

| | | | | |
|---|---|---|---|---|
| 3,506,982 | A * | 4/1970 | Steffee | C08L 27/18 |
| | | | | 623/21.16 |
| 7,037,342 | B2 * | 5/2006 | Nilsson | A61F 2/30756 |
| | | | | 623/21.15 |
| 9,452,057 | B2 * | 9/2016 | Dacosta | A61F 2/4644 |
| 2011/0093084 | A1 * | 4/2011 | Morton | A61B 17/15 |
| | | | | 623/21.19 |
| 2020/0107937 | A1 * | 4/2020 | Denham | A61F 2/4225 |
| 2021/0113344 | A1 * | 4/2021 | Bailey | A61B 17/1697 |

FOREIGN PATENT DOCUMENTS

FR          2828092 A1 * 2/2003 ........... A61F 2/4241

* cited by examiner

*Primary Examiner* — David H Willse
*Assistant Examiner* — Javier G Blanco
(74) *Attorney, Agent, or Firm* — Brennan, Manna & Diamond, LLC

(57) ABSTRACT

An MTP joint fusion device is disclosed which stabilizes the fusion site without the use of a fusion plate. Further, the MTP joint fusion device comprises an MTP head replacement component placed over the distal end of the first metatarsal. This portion of the device contains the bone ingrowth matrix. An intramedullary screw is driven through the distal central portion of the device into the base of the proximal phalanx of the hallux. At least two metatarsal screws are driven radially through the device into the metatarsal neck area. This secures the MTP head replacement component to the metatarsal at a specifically determined angle. Thus, the MTP joint fusion device provides for a more secure fusion environment, increased capacity for bone ingrowth, less potential for irritation from retained hardware, and earlier weight bearing as compared to traditional methods.

11 Claims, 2 Drawing Sheets

STAND ALONE METATARSOPHALANGEAL (MTP) JOINT FUSION DEVICE

BACKGROUND

The present invention relates generally to a medical device for use with the foot. More particularly, the present invention relates to a stand-alone metatarsophalangeal (MTP) joint fusion device that (a) fuses the MTP joint without the use of a plate, (b) allows the hallux (i.e., great toe) to be positioned in an anatomically functional position, and (c) restores length of the first ray lost due to a previously failed implant or non-union of a prior attempt at fusion of the MTP joint.

A first MTP joint fusion is typically performed to address painful arthritis of the first MTP joint, which is also known as late stage or severe hallux rigidus. An MTP joint fusion can also be utilized as a deformity corrective procedure in patients with severe bunions, or hallux valgus. By way of background, a bunion (hallux valgus) is a multi-planar angular deformity of the first MTP joint. This deformity often causes abnormal fitting of shoes, causing irritation of the skin in places which often leads to inflammation and pain. The bunion is caused by a malalignment of the first metatarsal and the proximal phalanx of the hallux, which, in turn, alters the distribution of ground reactive forces throughout the human gait cycle which can lead to irritation, calluses, blistering and ulceration of the skin. Malalignment of the first MTP joint for a sustained period of time will also eventually lead to degenerative changes or arthritis of the joint, which, in turn, can lead to pain, stiffness, inflammation, and difficulty maintaining a normal gait pattern.

The goal of fusion surgery is to align the hallux in a functional position, and to fuse the MTP joint. This eliminates painful motion created by the arthritic joint surfaces. To achieve fusion of the joint, any residual cartilage is removed from both joint surfaces and the underlying subchondral bone is prepared for fusion with fenestration—or drilling the bone to create tiny channels for bleeding to occur. The hallux is then positioned in a manner which optimizes gait function and the patient's ability to wear a shoe without difficulty. This is typically done with the hallux positioned so that it gently purchases the weight bearing surface when standing. The prepared joint is typically fused with one or two compression screws placed obliquely across the joint with a neutralization plate spanning the fusion site dorsally.

Typically, in order to correct a bunion deformity, an osteotomy is made in the metatarsal which allows the head of the metatarsal to be translated laterally in the transverse plane which realigns the MTP joint. The osteotomy is then fixated with cortical compression screws. More specifically, an incision is made at the dorsal joint surface, and the residual cartilage is removed from the metatarsal head and phalangeal base. The surgeon will typically create a "ball and socket" configuration of the surfaces using a variety of instrumentation. With the joint surfaces prepared and positioned appropriately, one or more compression screws are then placed across the joint, and the dorsal plate is applied. After implantation of the above referenced hardware, the surgical site is closed with retained sutures and the foot and lower leg are then typically placed into a splint during the healing process.

While traditional methods of primary first MTP joint fusion have proven to be effective, there are identifiable shortcomings when this type of fixation is utilized while attempting to maintain proper alignment of the hallux and restore anatomic length of the first ray after a failed prior attempt at fusion or the use of a joint sparing implant. More specifically, shortening of the joint may result, as it is necessary to resect non-viable bone and tissue at the non-union site in order to create an environment conducive to healing and bony bridging. Typically, a block of bone, either transplanted from the surgical patient (autograft), or cadaveric bone (allograft) is utilized. These methods generally do not create an ideal lattice structure to facilitate bony ingrowth. Further, the traditional use of the neutralization plate creates bulk in the soft tissue layer, which can be a source of irritation for the patient when shoes or other footwear is worn. Positioning of the hallux in the sagittal plane is critical, and the use of a straight plate to assist with the fusion can be difficult. Therefore, the plate frequently needs to be bent to accommodate the appropriate position of the hallux. However, bending of the plate can lead to premature failure, as well as affect the manner in which the affixing locking screws lock into the plate.

Therefore, there exists a long felt need in the art for a device and an improved method of fusing an MTP joint (a primary or revision fusing), or correcting a severe bunion deformity, that achieves restoration of length to the metatarsal during a revision surgery. There is also a long felt need in the art for a fusion device and an improved method of fusing an MTP joint that provides an appropriate structural lattice for bony ingrowth.

The present invention discloses an MTP joint fusion device which stabilizes the fusion site without the need for a fusion plate, and that allows for appropriate positional manipulation of the hallux during the surgery. The MTP joint fusion device of the present invention also provides restoration of lost length of the first ray secondary to failed fusion attempts or explanation of a joint implant from an attempted joint salvage procedure. More specifically, the MTP joint fusion device comprises an MTP head replacement construct placed over the distal end of the first metatarsal, and that contains a bone ingrowth matrix. An intramedullary screw is driven through the distal central portion of the device and into the base of the proximal phalanx of the hallux, and screws are driven radially through the device into the metatarsal neck area. This secures the fusion device at a specifically determined angle, relative to the metatarsal. In this manner, the MTP joint fusion device of the present invention provides for (a) a more secure fusion environment, (b) increased capacity for bone ingrowth, (c) less potential for irritation from retained hardware, and (d) earlier weight bearing for the patient, as compared to traditional methods.

SUMMARY

The following presents a simplified summary in order to provide a basic understanding of some aspects of the disclosed innovation. This summary is not an extensive overview, and it is not intended to identify key/critical elements or to delineate the scope thereof. Its sole purpose is to present some concepts in a simplified form as a prelude to the more detailed description that is presented later.

The subject matter disclosed and claimed herein, in one aspect thereof, comprises a stand-alone MTP joint fusion device which fuses the MTP joint without the need for or the use of a plate. The MTP joint fusion device is an intramedullary fixation device that comprises an MTP head replacement component and an intramedullary screw that is inserted into and protrudes from the center of the MTP head replacement component through an aperture at its distal end. The MTP head replacement component is preferably a generally domed shaped construct that is placed over the first metatarsal. The intramedullary screw is then driven down the distal phalanx from the center of the MTP head replacement component and secured.

In a preferred embodiment, the MTP joint fusion device further comprises at least two or a maximum of four radially located metatarsal screws which are inserted through a plurality of apertures positioned in the proximal end of the MTP head replacement component. The metatarsal screws are driven radially into the metatarsal to secure the MTP head replacement component onto the first metatarsal.

In a further preferred embodiment of the present invention, the MTP joint fusion device comprises a plurality of pointed trocar tips positioned on the distal part of the domed MTP head replacement component. The plurality of pointed trocar tips penetrate the distal phalanx to prevent it from rotating, and act to further secure the MTP head replacement component to the distal phalanx.

In yet another embodiment of the present invention, the MTP joint fusion device is manufactured as an additively printed titanium MTP head replacement component. Further, the MTP head replacement component comprises a bone growth promoting matrix. The use of a bone growth promoting matrix will allow for a more secure fusion and higher quality bone growth over the surgical site, which will result in better patient outcomes and an accelerated healing process.

To the accomplishment of the foregoing and related ends, certain illustrative aspects of the disclosed innovation are described herein in connection with the following description and the annexed drawings. These aspects are indicative, however, of but a few of the various ways in which the principles disclosed herein can be employed and is intended to include all such aspects and their equivalents. Other advantages and novel features will become apparent from the following detailed description when considered in conjunction with the drawings.

DETAILED DESCRIPTION

Figure 1:
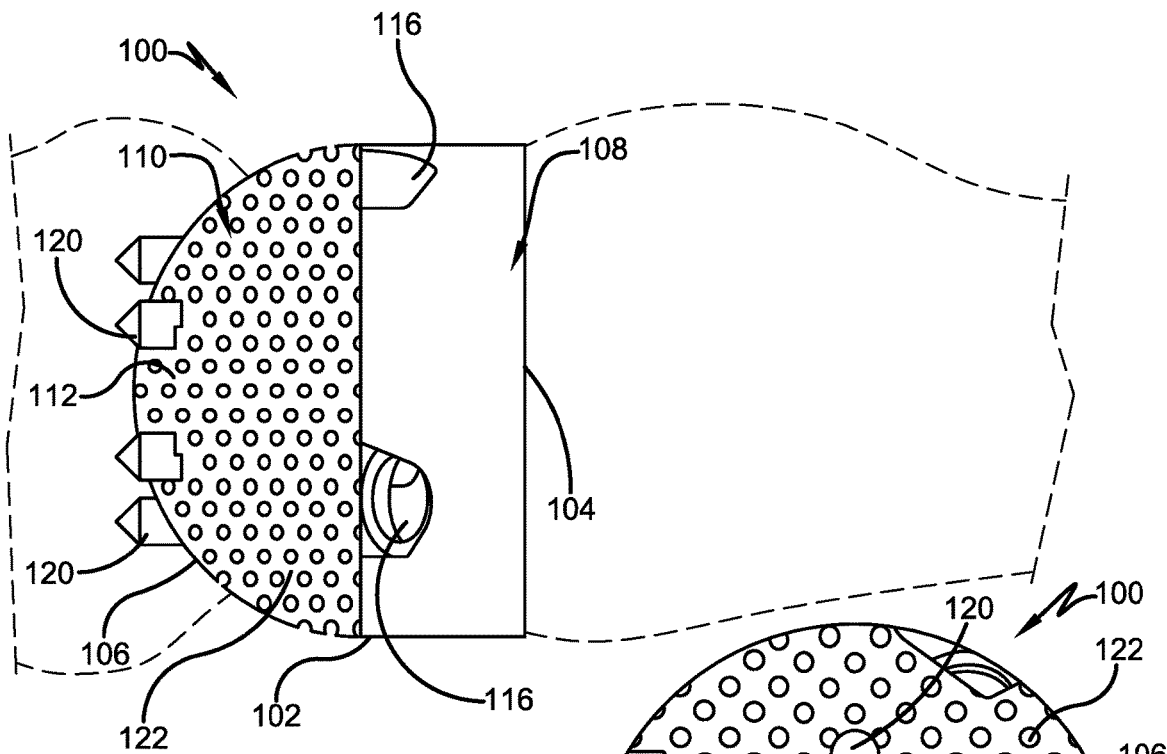
FIG. 1 illustrates a side perspective view of one possible embodiment of the MTP joint fusion device of the present invention disclosing a generally domed shaped MTP head replacement component in accordance with the disclosed architecture.

The innovation is now described with reference to the drawings, wherein like reference numerals are used to refer to like elements throughout. In the following description, for purposes of explanation, numerous specific details are set forth in order to provide a thorough understanding thereof. It may be evident, however, that the innovation can be practiced without these specific details. In other instances, well-known structures and devices are shown in block diagram form in order to facilitate a description thereof.

The present invention discloses a stand-alone MTP joint fusion device which fuses the MTP joint without the use of a plate, allows a toe to be fused in a dorsal or plantar location, and replaces the length of the metatarsal lost due to a previously failed implant. Further, the MTP joint fusion device comprises an MTP head replacement component placed over the first metatarsal, which has a bone growth promoting matrix thereon. An intramedullary screw is then driven down the distal phalanx from the center of the MTP head replacement component, and at least two metatarsal screws are then driven radially into the metatarsal to secure the MTP head replacement component so that the distal phalanx is positioned at a pre-determined angle to the metatarsal, said pre-determined angle preferably being between 0-20 degrees dorsal/plantar and abducted toward the $2^{nd}$ toe. Thus, the MTP joint fusion device provides for a more secure fusion and higher quality bone growth over the site, less irritation to the patient since a plate is not used, and the patient is able to bear weight on the affected bone structure sooner. Overall, the MTP joint fusion device provides for a replacement of the loss of length of the metatarsal caused by a previously failed implant and assists with bone growth, as well as provides a more secure fusion.

Figure 2:
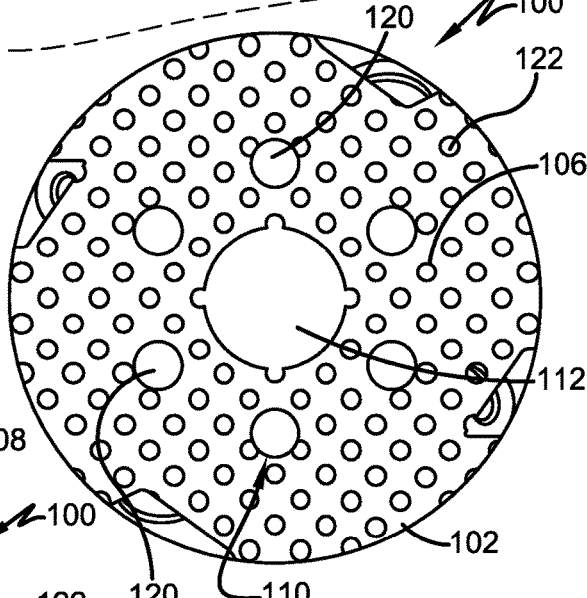
FIG. 2 illustrates a front perspective view of the MTP joint fusion device of FIG. 1 and disclosing the plurality of pointed trocar tips on the generally domed shaped MTP head replacement component in accordance with the disclosed architecture.
Figure 3:
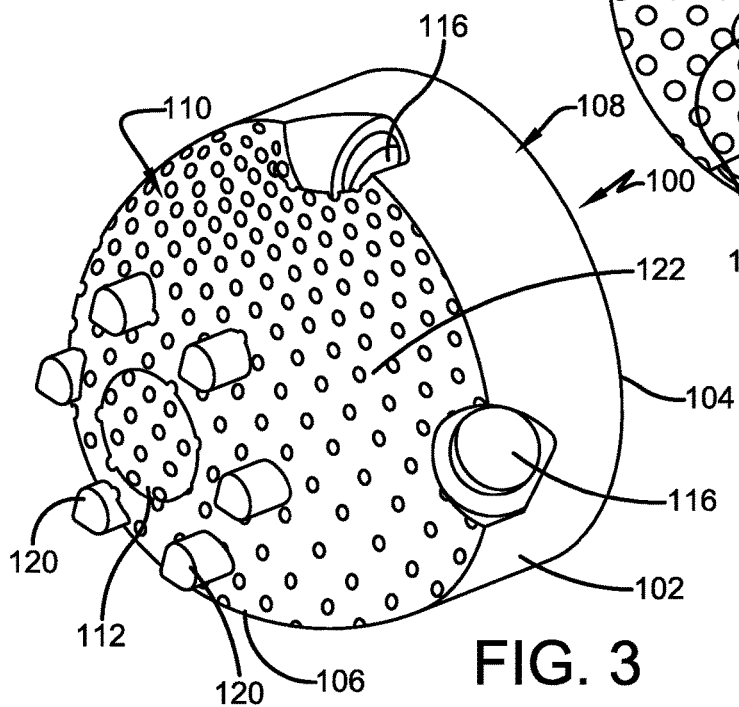
FIG. 3 illustrates a side perspective view of one possible embodiment of the MTP joint fusion device of the present invention and having a bone growth promoting matrix on the generally domed shaped MTP head replacement component in accordance with the disclosed architecture.

Referring initially to the drawings, FIGS. 1-3 illustrate the stand-alone metatarsophalangeal (MTP) joint fusion device 100 which fuses the MTP joint without the need for a surgical plate. More specifically, the MTP joint fusion device is an intramedullary fixation device which comprises an MTP head replacement component 102. The MTP head replacement component 102 is a generally domed shaped construct that is placed over the first metatarsal. Further, the MTP head replacement component 102 can be any suitable size, shape, and configuration as is known in the art without affecting the overall concept of the invention. One of ordinary skill in the art will appreciate that the shape and size of the MTP head replacement component 102 as shown in FIGS. 1-3 is for illustrative purposes only and many other shapes and sizes of the MTP head replacement component 102 are well within the scope of the present disclosure. Although dimensions of the MTP head replacement component 102 (i.e., length, width, and height) are important design parameters for good performance, the MTP head replacement component 102 may be any shape or size that ensures optimal performance during use, and may even be customized to fit the exact specifications/measurements of the patient's first metatarsal.

Additionally, the MTP head replacement component 102 comprises a proximal end 104 and a distal end 106, wherein the proximal end 104 comprises a concave opening 108 for engagement with the first metatarsal, and the distal end 106 comprises a generally rounded and dome-like structure 110 for engagement with the phalanx. Furthermore, the distal end 106 of the MTP head replacement component 102 comprises a continuous opening or aperture 112 at its center. The continuous aperture 112 is sized to receive an intramedullary screw 114. More specifically, the intramedullary screw 114 is inserted into and protrudes from the center of the MTP head replacement component 102 through the aperture 112 at its distal end 106. The intramedullary screw 114 is driven down the distal phalanx from the center of the MTP head replacement component 102 and secured to the distal phalanx.

Figure 4:
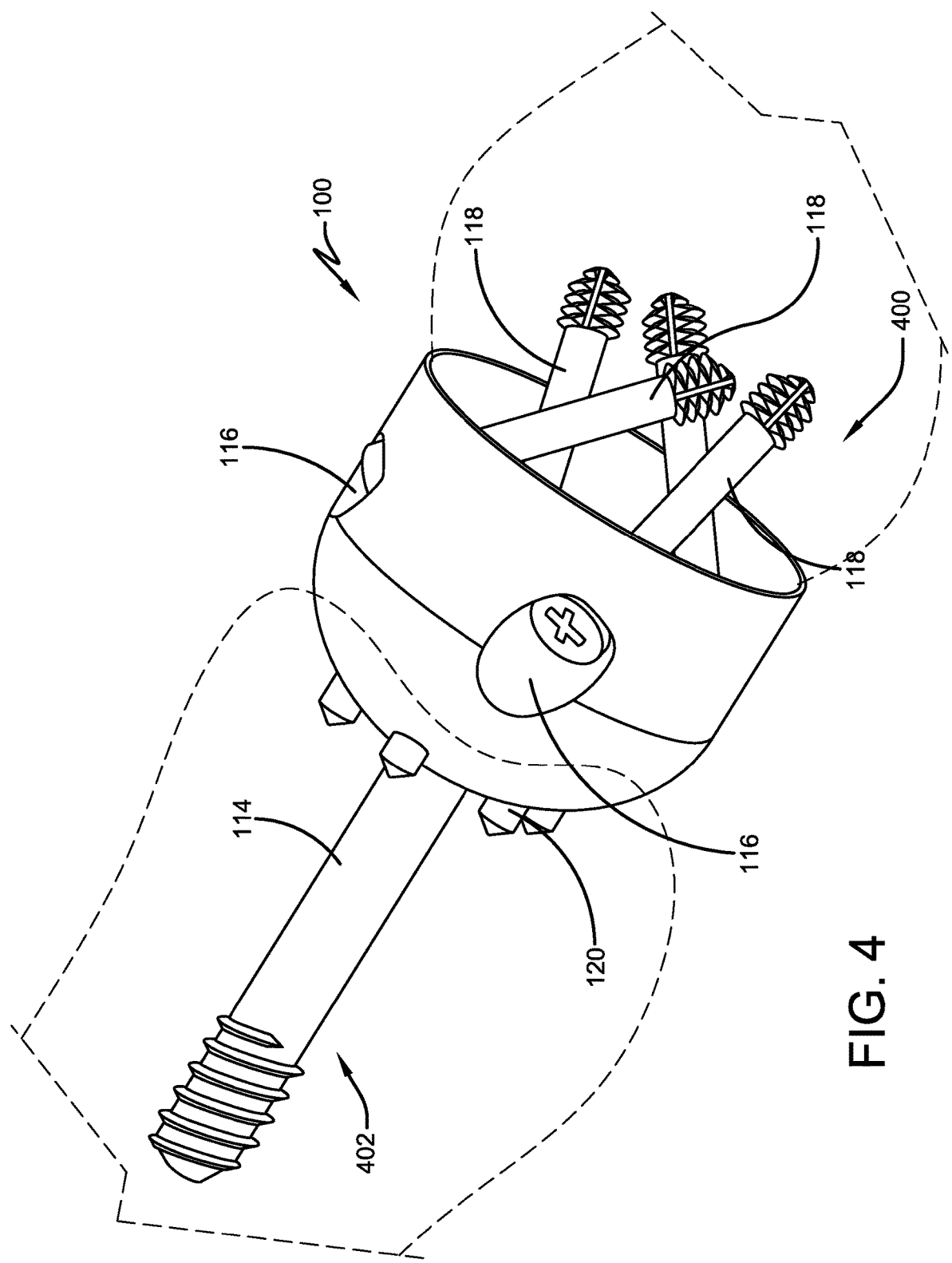
FIG. 4 illustrates a side perspective view of one possible embodiment of the MTP joint fusion device, intramedullary screw, and plurality of radially located metatarsal screws secured on the MTP joint in accordance with the disclosed architecture.

Further, the proximal end 104 of the MTP head replacement component 102 comprises a plurality of apertures 116 positioned around the circumference of the proximal end 104 of the MTP head replacement component 102, as best shown in FIGS. 3 and 4. The number of apertures 116 is typically four, but any other suitable number of apertures 116 can be used depending on the needs and/or wants of a user. The plurality of apertures 116 are sized to receive a plurality of metatarsal screws 118, as best shown in FIG. 4. In a preferred embodiment of the present invention, at least two and a maximum of four radially located metatarsal screws 118 are inserted through the plurality of apertures 116 positioned in the proximal end 104 of the MTP head replacement component 102 depending on the needs and/or wants of a user. The metatarsal screws 118 are driven radially into the metatarsal such that the metatarsal screws 118 do not intersect with one another, and act to further secure the MTP head replacement component 102 onto the first metatarsal (no shown).

Additionally, the distal end 106 of the MTP head replacement component 102 further comprises a plurality of pointed trocar tips 120 positioned on the distal part 106 of the domed construct (structure) 110. Specifically, the plurality of pointed trocar tips 120 are positioned radially around the aperture 112 located in the center of the distal end 106 of the MTP head replacement component 102. The plurality of pointed trocar tips 120 penetrate the distal phalanx to prevent it from rotating, and acts to further secure the MTP head replacement component 102 in place.

In a preferred embodiment, the MTP joint fusion device 100 is manufactured using additive manufacturing (AM) techniques and grown as one part. Specifically, the MTP joint fusion device 100 is additively printed and able to be manufactured in a variety of sizes as well as to be customizable to fit the exact specifications/measurements of the patient. Further, the MTP joint fusion device 100 is additively printed with titanium, but can be additively printed with any other suitable metal as is known in the art, as long as the metal is medical grade and able to be additively printed.

Additionally, the MTP head replacement component 102 comprises a bone growth promoting matrix 122, as best shown on FIGS. 1-3. The use of a bone growth promoting matrix 122 will allow for a more secure fusion and higher quality bone growth over the surgical site. The bone growth promoting matrix 122 can be shaped as a geometric design comprising shapes such as crosses, squares, and/or triangles in every direction, or shaped more of an organic design where the indices are random and protrude in all directions, at different angles and thicknesses. This geometric matrix 122 promotes bone growth within and around the surgical site, creating a more secure fusion of the MTP joint and accelerating the recovery process.

As best shown in FIG. 4, in operation, the MTP joint fusion device 100 is applied to the first metatarsal 400 of the foot. The goal of surgery is to make the great toe joint solidly aligned and immobile. This eliminates much of the pain associated with the arthritic joint since there will now be no motion through the arthritic joint. Specifically, an incision is made on top of the big toe. Any unnecessary cartilage is cleared away to allow the two bones to heal or fuse together. To fuse the great toe joint, any remnant cartilage on the arthritic joint surface is also removed and the surgeon uses a combination of instruments and tools to shape each bone for a perfect fit, which prepares the underlying bone for fusion.

Once prepared, an intramedullary screw 114 is inserted into the aperture 112 at the center of the distal end 106 of the MTP replacement head component 102. The phalanx 402 is then lined up with the distal end 106 of the MTP replacement head component 102 and the intramedullary screw 114 is then driven down the distal phalanx 402 from the center of the device 100. As the intramedullary screw 114 is driven down the distal phalanx 402, the head of the phalanx 402 engages the plurality of pointed trocar tips 120 on the distal end 106 of the MTP replacement head component 102 which act to further secure the MTP joint fusion device 100 onto the distal phalanx 402 and prevent the distal phalanx 402 from rotating.

Then, the proximal end 104 of the MTP joint fusion device 100 is positioned over the first metatarsal 400. The joint is then positioned in a manner that maximizes the walking ability and maintains acceptable clinical alignment. This is traditionally done with the toe positioned so that it just gently touches the ground in a weight-bearing position. Once the joint is correctly positioned, two to four metatarsal screws 118 are driven radially through the apertures 116 on the proximal end 104 of the MTP replacement head component 102 into the metatarsal 400 to secure the MTP joint fusion device 100 between the first metatarsal 400 and the distal phalanx 402.

What has been described above includes examples of the claimed subject matter. It is, of course, not possible to describe every conceivable combination of components or methodologies for purposes of describing the claimed subject matter, but one of ordinary skill in the art may recognize that many further combinations and permutations of the claimed subject matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A metatarsophalangeal (MTP) joint fusion device comprising:
    an MTP head replacement component which comprises a proximal end and a distal end;
    wherein the proximal end comprises a concave opening having a metatarsal-engaging surface for engagement with a first metatarsal and the distal end comprises a dome-like structure having a phalanx-engaging surface for engagement with a distal phalanx;
    wherein the distal end of the MTP head replacement component is sized and configured to be positioned at the distal phalanx and the proximal end of the MTP head replacement component is sized and configured to be positioned over the first metatarsal to secure the MTP head replacement component between the first metatarsal and the distal phalanx;
    wherein the MTP head replacement component comprises an aperture at a center of the distal end, wherein the aperture is sized to receive an intramedullary screw;
    wherein the MTP head replacement component comprises a plurality of apertures positioned around a circumference of the proximal end, wherein the plurality of apertures are sized to receive a plurality of metatarsal screws to secure the MTP replacement head component to the first metatarsal; and wherein the intramedullary screw is sized and configured to be driven down the distal phalanx from the aperture at the center of the distal end of the MTP head replacement component and sized and configured to be secured to the intramedullary canal of the distal phalanx.

2. The MTP joint fusion device of claim 1 wherein the plurality of apertures comprises four apertures.

3. The MTP joint fusion device of claim 2 wherein two metatarsal screws are secured radially in the plurality of apertures.

4. The MTP joint fusion device of claim 2 wherein three metatarsal screws are secured radially in the plurality of apertures.

5. The MTP joint fusion device of claim 1 wherein the MTP head replacement component comprises a plurality of pointed trocar tips positioned on the distal end.

6. The MTP joint fusion device of claim 1 wherein the MTP head replacement component comprises a bone growth promoting matrix.

7. The MTP joint fusion device of claim 1 wherein the MTP head replacement component is manufactured using additive manufacturing techniques.

8. The MTP joint fusion device of claim 7 wherein the MTP head replacement component is additively manufactured of titanium.

9. A metatarsophalangeal (MTP) joint fusion device comprising:
  an MTP head replacement component which comprises a proximal end and a distal end;
  wherein the proximal end comprises a concave opening having a metatarsal-engaging surface for engagement with a first metatarsal and the distal end comprises a rounded, dome-like structure having a phalanx-engaging surface for engagement with a distal phalanx;
  wherein the distal end of the MTP head replacement component is sized and configured to be positioned at the distal phalanx and the proximal end of the MTP head replacement component is sized and configured to be positioned over the first metatarsal to secure the MTP head replacement component between the first metatarsal and the distal phalanx;
  wherein the MTP head replacement component comprises a plurality of pointed trocar tips positioned on the distal part and an aperture at a center of the distal end, the aperture at the center of the distal end sized to receive an intramedullary screw;
  wherein the MTP head replacement component comprises a plurality of apertures positioned around a circumference of the proximal end, the plurality of apertures sized to receive a plurality of metatarsal screws;
  wherein the plurality of metatarsal screws are sized and configured to be driven radially into the first metatarsal such that the plurality of metatarsal screws do not intersect and act to further secure the MTP head replacement component onto the first metatarsal; and
  wherein the intramedullary screw is sized and configured to be driven down the distal phalanx from the aperture at the center of the distal end of the MTP head replacement component and sized and configured to be secured to the intramedullary canal of the distal phalanx.

10. The MTP joint fusion device of claim 9 wherein the MTP head replacement component is additively manufactured of titanium.

11. The MTP joint fusion device of claim 9 wherein the MTP head replacement component comprises a bone growth promoting matrix.

* * * * *